United States Patent [19]

Malmin

[11] 4,019,254
[45] Apr. 26, 1977

[54] ENDODONTIC OPERATING INSTRUMENT
[76] Inventor: Oscar Malmin, 127 E. Wayne Ave., Akron, Ohio 44301
[22] Filed: June 30, 1975
[21] Appl. No.: 591,693
[52] U.S. Cl. ................................................. 32/57
[51] Int. Cl.$^2$ .......................................... A61C 5/02
[58] Field of Search ..................... 32/57, 58, 59, 50
[56] References Cited
UNITED STATES PATENTS
1,067,015   7/1913   Fowler .................................. 32/57

OTHER PUBLICATIONS

Midwest American, Dental Division of American Hospital Supply, 1980 N. Hawthorne, Melrose Park, Ill.

Primary Examiner—Robert Peshock
Attorney, Agent, or Firm—Reese Taylor

[57] ABSTRACT

An endodontic operating instrument is disclosed for utilization in the preparation of root canals, either manually or in conjunction with ultrasonic or other instrumentation. The instrument per se includes an elongate shank of virtually any cross section desired and a handle or attachment means on one end so that the instrument may be operated manually by simply grasping the handle; operated by means of a conventional dental handpiece by simply attaching the attachment means thereto; or operated by means of an ultrasonic instrument. The instruments have a coating of abrasive material applied to at least a portion of their exterior surfaces to facilitate the preparation of the root canal by the action of the abrasive on the tooth.

4 Claims, 14 Drawing Figures

U.S. Patent  April 26, 1977  Sheet 1 of 2  4,019,254
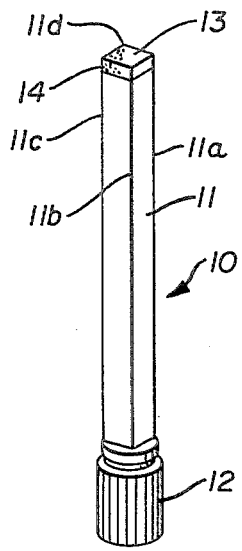
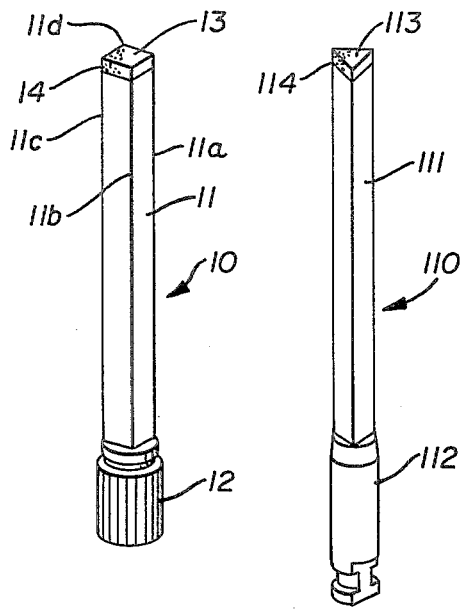
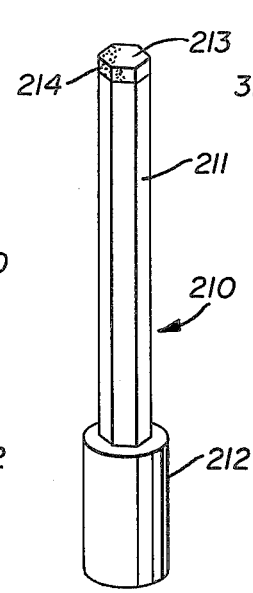
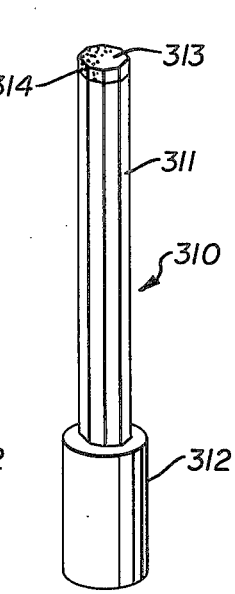
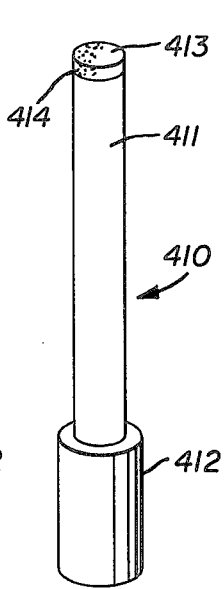
FIG. 1  FIG. 2  FIG. 3  FIG. 4  FIG. 5
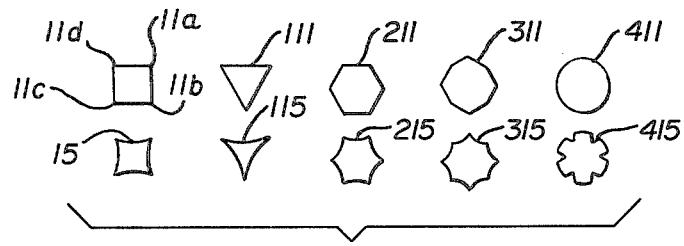
FIG. 6
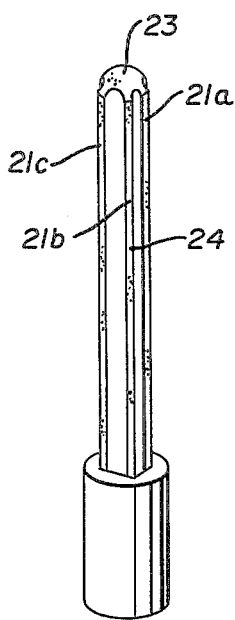
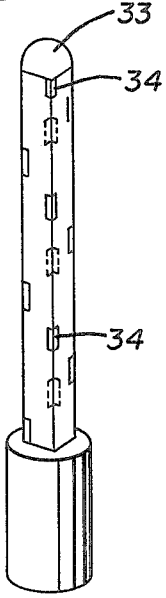
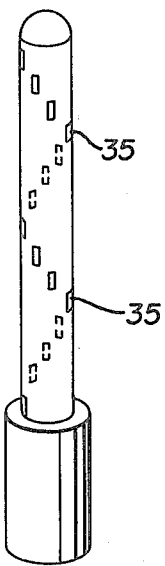
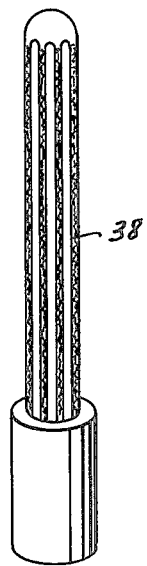
FIG. 7  FIG. 8  FIG. 9  FIG. 10

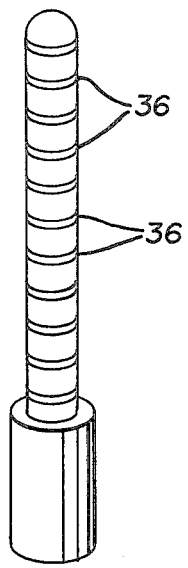
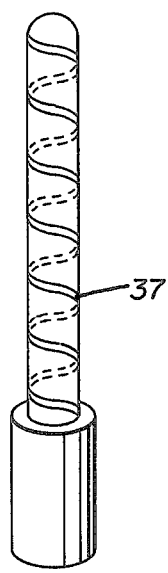
FIG. 11               FIG. 12
PRIOR ART
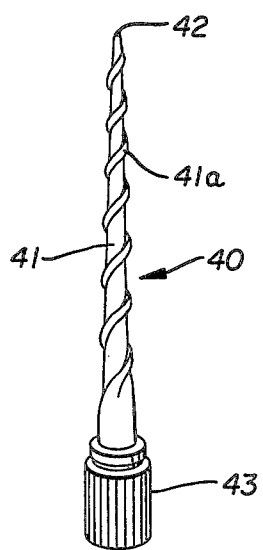
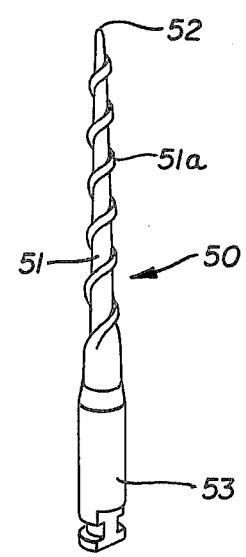
FIG. 13               FIG. 14

4,019,254

ENDODONTIC OPERATING INSTRUMENT

BACKGROUND OF THE INVENTION

This invention relates, in general, to instruments utilized in endodontic treatment, primarily the preparation of root canals for filling. Representative instruments of this type are shown in Applicant's earlier U.S. Pat. Nos. 3,772,791 and 3,855,702. This invention, in particular, relates to an improved instrument having a quantity of abrasive material secured to its surface.

DESCRIPTION OF THE PRIOR ART

The prior art consists of many instruments designed to facilitate root canal preparation, several of which are illustrated in Applicant's earlier patents noted above. Further examples of this type of instrument are also shown in FIGS. 13 and 14 of the drawings. In general the prior art instruments are made by drawing a triangular or square piece of tempered steel wire down to a tapered configuration while at the same time twisting the wire to produce a threaded or fluted type construction. Instruments of this type can normally only be operated efficiently in a rotary manner because of the screwlike nature of their external configuration. Instruments of this type also are inherently prone to fracture due to stresses induced during production, and furthermore the screw-like configuration tends to bind or lock in the walls of the root canal, and the actual operative effect of the instrument on the material of the canal walls is to "chip" rather than to "mill."

Additionally, the known forms of instruments in this field can generally be used only in a manual or motorized rotary or reciprocal vertical action due to their inherent structural limitations.

Furthermore, the present instruments are generally sharply pointed at the outboard end thereof and have a tendency, by virtue of this sharp point, to create their own pathway through the tooth rather than following the natural contours of the rool canal. This creates the possibility of lateral perforation of the root and potential loss of the tooth.

There are also other conventional forms of instruments utilized in endodontics, such as files, which utilize a rasping action in the root canal. By their very nature these can only be used with a push-pull type movement, and generally, since they rely on the blade edges for reducing the root canal structure, the blades are tempered, and this tempering tends to increase the brittleness thereof and thereby the propensity toward binding or breaking of the instrument in the canal.

SUMMARY OF THE INVENTION

It has been found that an improved endodontic operating instrument can be provided if the instrument is provided with an elongate shank having grasping or attachment means at one end and, furthermore, if the shank is provided in selected areas thereon with abrasive material such as diamond bort or other similar abrasives. By virtue of the application of the abrasive material, the milling action which takes place in the root canal is no longer entirely dependent upon the sharpness and hardness of the blade edges, and therefore it is not necessary to temper the instrument and greater ductility is achieved, thereby minimizing the chances of breakage of the instrument within the root canal.

It has also been found that by making the outboard end of the shank in a blunt or rounded configuration, the dangers of perforating the side walls of the canal are minimized.

Furthermore, by providing the abrasive and relying upon its qualities to operate on the tooth material, a very fine powder is generated in the canal in comparison with the varying sized chips which are generally generated in the prior art. This is much easier to remove from the canal by irrigating means due to the relatively small size of the particles which will neither obstruct the irrigating cannula nor the root canal itself.

It has also been discovered that grasping and attachment means can be applied to one end of the shank so that the instrument can be operated either manually, by means of a dental handpiece, or by means of an ultrasonic dental unit.

Accordingly, production of an improved endodontic instrument of the character above-described becomes the principal object of this invention, with other objects thereof becoming more apparent upon a reading of the following brief specification and claims, considered and interpreted in view of the accompanying drawings.

OF THE DRAWINGS

FIG. 1 is a perspective view of one form of the instrument.

FIGS. 2 through 5 are perspective views of other forms of the instrument having differing cross-sectional configurations to the shank portion.

FIG. 6 respresents a series of end views of the shanks of FIGS. 1 through 5 showing various cross-sectional configurations.

FIGS. 7 through 10 are perspective views showing how the abrasive material is applied to various areas on the shanks.

FIG. 11 is a perspective view showing a modified form of the invention with a different application pattern for the abrasive material.

FIG. 12 is a perspective view showing yet another modified pattern of application of the abrasive material.

FIGS. 13 and 14 are a perspective view of conventional prior art instruments.

BRIEF DESCRIPTION OF THE PREFERRED EMBODIMENTS

Before turning to a discussion of the improved instrument illustrated in here, reference is called to FIGS. 13 and 14 of the drawings showing conventional prior art instruments.

For example, FIG. 13 shows an instrument 40 having an elongate shank 41 which tapers to a pointed tip 42 at one end. The body of the shank carries spiral screw-type flutes 41a, and a grasping member 43 is secured to the opposed end of shank 41. This particular type of instrument is intended to be operated manually by grasping the shank 43 and rotating the instrument to chip away the material from the walls of the root canal.

FIG. 14 shows a similar instrument 50 having an elongate shank 51 and fluted areas 51a, with the shank tapering to a pointed tip 52 and with an attachment member 53 being secured to the opposed end of the shank 51. This particular instrument is for utilization with a motorized handpiece, and the attachment means 53 can be snapped into the handpiece in conventional fashion. Once more, the motion is rotary. It should be noted that at the present time Applicant is unaware of any ultrasonically activated root canal instruments of this particular type. It is prior art such as this that the present invention is intended to be an improvement over.

In view of the fact that a number of different cross-sectional configurations are illustrated in FIGS. 1 through 5, only FIG. 1 will be described in detail, with it being understood that similar reference numbers are applicable to similar features on the forms shown in FIGS. 2 through 5.

Accordingly then, referring to FIG. 1, the improved instrument, generally indicated by the numeral 10, has an elongate shank 11 and a grasping means 12 secured to one end thereof. The grasping means 12, as illustrated, is intended to be utilized by grasping it manually and resembles the member 42 of FIG. 13. It should be noted here that an attachment means such as indicated at 112 in FIG. 2 could be substituted, if desired, so that the device can be attached to a motorized handpiece. No detailed description of these means will be made since they are conventional in nature, but it is noted that the present invention can be activated by any known means. Therefore, the "grasping means" of the forms of the invention shown in FIGS. 3 through 12 have been illustrated in schematic fashion only. In view of this fact, the term grasping means as used herein is intended to define the various known means just described.

Referring again to FIG. 1, in the form of the invention shown therein, the cross-sectional configuration of the shank 11 is essentially square, thereby presenting a plurality of blade edges 11a, 11b, 11c, and 11d. The end of the shank 11, indicated by the numeral 13, is, as will be noted, blunt, rounded, or chamfered and carries a quantity of abrasive material 14 thereon.

FIGS. 2 through 5 show similar instruments, with the principal differences being the cross-sectional configuration thereof, ranging from the triangular cross section of FIG. 2 to the circular cross section of FIG. 5. The instruments, however, all have the common characteristic of the abrasive material secured to the blunt end thereof and, except for FIG. 5, providing milling blade edges.

FIGS. 7 through 10 show further variations on the cross-sectional configuration in which the abrasive material is applied, for example, in FIG. 7 not only to the rounded or blunt end 23, but also to the blade edged 21a, 21b, and 21c.

Additionally, in FIG. 8 the abrasive material 34 is applied in a random type arrangement, while in FIG. 9 the material 35 is applied in a helical arrangement.

In FIGS. 11 and 12 the arrangement of the abrasive material differs somewhat from that of FIGS. 8 and 9, for example. Thus in FIG. 11 the material is applied in a series of annular rings 36, while in FIG. 12 it is in a continuous spiral pattern as indicated by the numeral 37.

All of these forms of the invention have in common the fact that no longer is the sharpness of the blade edges being relied upon solely for operation within the root canal because the abrasive material, by its action and pattern of varying distribution, prepares the walls of the root canal as the instrument is agitated therein. The abrasive material 14, 24, 34, 35, for example, actually mills out the canal, and accordingly a greatly improved operation is made possibly by this structure. Furthermore, by virtue of the fact that the conventional configuration is no longer being utilized, the instrument can be used utilizing any form of motivation mentioned above such as, for example, ultrasonic activation. Thus the structural limitations of the instrument no longer limit the mode of operation.

It should be noted here that while only a flat end or a rounded end has been illustrated, any configuration could be utilized, but it is desirable if the pointed tip of the prior art is avoided and the distal end is basically blunt.

Furthermore and referring to FIGS. 1 through 7 and 10, it will be noted that it is also possible to hollow out the areas between the blade edges such as 11a and 11b as, for example, at 15 in FIG. 6. This permits the material which is ground or milled off of the tooth to be aspirated out along the length of the shank, thereby avoiding packing it into the canal and thereby making it possible to much more efficiently operate within the root canal.

Thus the distribution patterns of the abrasive bort which are illustrated as being selectively applied in FIGS. 1 through 12 are designed to avoid the possibility of binding or freezing the instrument due to approximating diameters of the root canal and the instrument. However, while certain illustrative patterns are illustrated, it is understood that the shank may contain patterns of distribution of the abrasive bort varying from minimal to total coverage of the shank without departing from the spirit of this concept.

Also, while the motive means of employing the instruments of this invention have been designated as hand or manual manipulation, motorized or gear-driven, and ultrasonic activation, it is understood that the instruments of this invention can be employed equally effectively with any form or energy source capable of movement motivation of the instruments.

It should also be noted that the dimensions of the instruments of FIGS. 1 through 12 have been exaggerated for purposes of illustration, and that the actual instruments are much smaller than the illustrations.

Accordingly, while a full and complete description of the invention has been set forth in accordance with the dictates of the Patent Statutes, modifications may be resorted to without departing from the spirit hereof or the scope of the appended claims.

What is claimed is:

1. An endodontic instrument for insertion into a root canal, comprising:
   A. an elongate flexible shank;
   B. grasping means carried on one end of said shank;
   C. the remaining end of said shank being blunt; and
   D. a quantity of abrasive material carried by said blunt end of said shank
      1. whereby said blunt end of said shank may form a seat in said root canal for reception of endodontic sealing material.

2. An endodontic instrument for insertion into a root canal, comprising,
   A. an elongate bendable shank;
   B. grasping means carried on one end of said shank; and
   C. abrasive material carried by only a portion of the surface of said shank;
   D. said shank having a cross-sectional configuration such that at least one longitudinally extending, substantially straight blade edge is presented; and
   E. said abrasive material being carried by only the blade edge 1. whereby said instrument may mill the interior of the root canal and reduce the material thus milled to a relatively fine powder.

3. An endodontic instrument for insertion into a root canal, comprising;
  A. an elongate bendable shank;
  B. grasping means carried on one end of said shank; and
  C. abrasive material carried by at least a portion of the surface of said shank
  D. said abrasive material being carried by said shank in a helical pattern about the periphery thereof
    1. whereby said instrument may mill the interior of the root canal and reduce the material thus milled to a relatively fine powder.

4. An endodontic instrument for insertion into a root canal, comprising;
  A. an elongate bendable shank;
  B. grasping means carried on one end of said shank; and
  C. abrasive material carried by only the a portion of the surface of said shank;
  D. said abrasive material being carried by the surface of said shank in a random pattern
    1. whereby said instrument may mill the interior of the root canal and reduce the material thus milled to a relatively fine powder.

* * * * *